United States Patent
Wu et al.

(10) Patent No.: US 11,698,357 B2
(45) Date of Patent: Jul. 11, 2023

(54) METHOD FOR SCREENING, ISOLATING AND PURIFYING ANALYTES

(71) Applicant: CHANG GUNG UNIVERSITY, Taoyuan (TW)

(72) Inventors: Min-Hsien Wu, Taoyuan (TW); Po-Yu Chu, Taoyuan (TW); Wen-Pin Chou, Taoyuan (TW); Chia-Jung Liao, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 1002 days.

(21) Appl. No.: 16/503,854

(22) Filed: Jul. 5, 2019

(65) Prior Publication Data
US 2020/0240950 A1 Jul. 30, 2020

(30) Foreign Application Priority Data
Jan. 25, 2019 (TW) .................. 108102977

(51) Int. Cl.
*G01N 27/447* (2006.01)
*G01N 33/50* (2006.01)
*C12Q 1/24* (2006.01)

(52) U.S. Cl.
CPC ......... *G01N 27/44704* (2013.01); *C12Q 1/24* (2013.01); *G01N 33/5014* (2013.01); *G01N 33/5017* (2013.01); *G01N 33/5091* (2013.01); *G01N 33/5097* (2013.01); *G01N 2510/00* (2013.01); *G01N 2800/44* (2013.01); *G01N 2800/52* (2013.01)

(58) Field of Classification Search
CPC ......... G01N 27/44704; G01N 33/5014; G01N 33/5017; G01N 33/5091; G01N 33/5097; G01N 2510/00; G01N 2800/44; G01N 2800/52; C12Q 1/24; C12Q 1/025; B03C 5/005
See application file for complete search history.

(56) References Cited

U.S. PATENT DOCUMENTS

2009/0170186 A1* 7/2009 Wu .................. B01L 3/502761
435/286.1

FOREIGN PATENT DOCUMENTS

WO WO-2018209145 A1 * 11/2018 ........... C12Q 1/6827

OTHER PUBLICATIONS

Po-Yu Chu et al., "The Utilization of an Accelerating Moving Light Image in an Optically-Induced Dielectrophoresis (ODEP)-Based Microfluidic System for the Isolation of Cancer Cells With Different Responses to the Cytotoxic Effect of Anti-Cancer Drugs", Nov. 11-15, 2018, Chang Gung University, Taiwan.
Po-Yu Chu, et al., "The Utilization of an Accelerating Moving Light Image in an Optically-Induced Dielectrophoresis (ODEP)-Based Microfluidic System for the Isolation of Cancer Cells With Different Responses to the Cytotoxic Effect of Anti-Cancer Drugs", Nov. 30, 2018-Dec. 1, 2018, Chang Gung University, Taiwan.

(Continued)

*Primary Examiner* — Jennifer Wecker
*Assistant Examiner* — Michael Paul Shimek
(74) *Attorney, Agent, or Firm* — WPAT, PC

(57) ABSTRACT

The present disclosure provides a method for screening, isolating and purifying analytes.

6 Claims, 18 Drawing Sheets
(1 of 18 Drawing Sheet(s) Filed in Color)

(56) References Cited

OTHER PUBLICATIONS

Po-Yu Chu et al., "Utilization of optically induced dielectrophoresis in a microfluidic system for sorting and isolation of cells with varied degree of viability: Demonstration of the sorting and isolation of drug-treated cancer cells with various degrees of anti-cancer drug resistance gene expression", Sensors & Actuators: B. Chemical 283 (2019) 621-631.

* cited by examiner

METHOD FOR SCREENING, ISOLATING AND PURIFYING ANALYTES

CROSS-REFERENCE TO RELATED APPLICATION

This application claims priority of Taiwan patent application No. 108102977, filed on Jan. 25, 2019, the content of which is incorporated herein in its entirety by reference.

BACKGROUND OF THE INVENTION

1. Field of the Invention

The present invention relates to a method for screening, isolating and purifying analytes.

2. The Prior Art

The degree of cell viability, as an important marker for evaluating the physiology status of cells, may show detectable differences by variations of environmental factors. In particular, due to differences in gene expression among cells, the cells with the same genotype may also express different environmental tolerances, which can be distinguished by measuring the differences in the degree of cell viability. For example, drug resistance of tumors is often considered as a key factor of clinical chemotherapy failure. However, in the early stages of tumor development, tumor cells with drug resistance only account for a small part of whole tumor tissues. Meanwhile, under normal circumstances, because the physiological characteristics of the tumor cells with drug resistance are not significantly different from those of tumor cells without drug resistance, it makes the drug resistance difficult to be detected in the early stage of tumor tissue. However, once an anti-cancer drug is administered, tumor cells without or with drug resistance would exhibit significant differences in their degree of cell viability, making tumor cells with drug resistance easy to be distinguished. Therefore, through regulating the culture environment of cells (e.g., treatment of drugs, radiation, oxidative stress, toxic chemicals or cell apoptosis), cell populations with high environmental tolerance can be distinguished by measuring the variations in the degree of cell viability.

Conventional methods for isolating cells with different degrees of cell viability mostly rely on differences in cell size or surface antigens. However, changes in the physiological state of cells (e.g., cell viability) do not necessarily result in a significant change in cell size and surface antigens. Therefore, conventional methods do not effectively distinguish cells with different degrees of cell viability. On the other hand, the pretreatment process of antibody labeling is lengthy and costly, and it may cause changes in cell status and gene expression. Therefore, the label-free methods have been proposed to separate cells with different degrees of cell viability.

The aqueous two-phase system (ATPS) and dielectrophoresis (DEP) are two commonly used label-free methods for separating cells. ATPS mainly uses the difference in affinity of biomolecules for different solution media to separate cells. For example, due to the high hydrophobicity of the live cell surface, live cells would move toward a high PEG solution phase in a weakly acidic ATPS environment composed of polyethylene glycol (PEG) and Dextran. By contrast, dead cells have no such tendency. Therefore, the microfluidic system integrated with ATPS can effectively separate the live and dead cells. However, ATPS-based methods cannot perform a more precise separation of cells with different physiology status (e.g., isolation of cells expressing varying levels of drug resistant genes). On the other hand, the DEP-based system can be utilized to facilitate cell polarization via a non-uniform alternating electric (AC) field. Meanwhile, due to the differences in dielectric and conductivity of cell membrane and the cytoplasm, the strength of DEP-induced cell polarization would change under different cell physiological conditions, making the DEP-based system utilized to identify and separate cells with different physiological states. Through the integration with the microfluidic system, a large number of metal electrodes-based DEP platforms were developed for live and dead cell separation and applied to the separation of bacteria, yeast, and blood cells. However, the conventional solid-state metal electrode-based DEP platform has obvious disadvantages, such as the cumbersome manufacturing in a chip, lack of flexibility in operation, and high cost in production.

Therefore, those skilled in the art urgently need to develop a novel method for screening, isolating and purifying an analyte, thereby overcoming the disadvantages of the prior art and benefiting people in need thereof.

SUMMARY OF THE INVENTION

A primary objective of the present invention is to provide a method for screening, isolating and purifying an analyte by using an optically induced-electrophoresis (ODEP) device, the method comprising the steps of: (a) performing a treatment on the analyte to obtain a treated analyte; (b) introducing the treated analyte into the optically induced-electrophoresis device, wherein the optically induced-electrophoresis device comprises a main microchannel, at least one side microchannel, at least one target collection tank, and an optically-induced dielectrophoretic force light image module having a controllable velocity, and the optically-induced dielectrophoretic force light image module screens the treated analyte in the main microchannel in order to separate the treated analyte into at least one target using a separation and purification method; and (c) collecting the at least one target into the at least one target collection tank.

According to an embodiment of the present invention, the method is used for screening a size or a degree of viability of the analyte, and isolating and purifying the analyte having different sizes or degrees of viability.

According to an embodiment of the present invention, the analyte is a microorganism, a plant cell, an animal cell, a chemical material particle or a metal particle.

According to an embodiment of the present invention, the treatment is a treatment capable of inducing a viability difference of cells, or a treatment capable of inducing a size difference of the cells, the chemical material particle or the metal particle.

According to an embodiment of the present invention, the treatment is a drug treatment, a radiation treatment, an oxidative stress treatment, a toxic chemical treatment, or a cell apoptosis treatment when the treatment is capable of inducing the degree of the viability difference of cells.

According to an embodiment of the present invention, the optically-induced dielectrophoretic force light image module comprises at least one first moving light bar, the at least one first moving light bar has a moving velocity of a light image ranging from 0.01 μm/s to 1 cm/s, and the moving velocity of the light image is a variable speed.

According to an embodiment of the present invention, the optically-induced dielectrophoretic force light image module comprises a plurality of second moving light bars, each of the plurality of second moving light bars has a moving velocity of a light image ranging from 0.01 µm/s to 1 cm/s, the moving velocity of the light image among the plurality of second moving light bars is different, and the moving velocity of the light image is a constant speed.

According to an embodiment of the present invention, the separation and purification method is performed by a physical drive selected from the group consisting of: a fluid drive, an electromagnetic drive, an optical drive, and an optically-induced dielectrophoretic force drive.

According to an embodiment of the present invention, the method is further used for screening, isolating and purifying cells having different degrees of environmental tolerance gene expression.

According to an embodiment of the present invention, the environmental tolerance gene is a drug-associated gene, a radiation-associated gene, an oxidative stress-associated gene, a toxic chemical-associated gene, or a cell apoptosis-associated gene.

In summary, the present invention providing a method for screening, isolating and purifying an analyte has the benefits on simple and flexible operation, and high sensitivity, resolution, and precision. The method of the present invention can successfully screen the analytes via the size or the viability degree. Meanwhile, the method of the present invention can isolate and purify the analytes with different sizes or various degrees of viability to facilitate identification of cell populations with different degrees of environmental tolerances (e.g., drug resistance, radiation resistance, oxidative stress resistance, toxic chemical resistance, or cell apoptosis degrees) or different sizes of chemical material particles or metal particles. Furthermore, the method of the present invention can be used as a front-end screening instrument for subsequent research analysis or clinical applications and can make immediate adjustments according to different sample conditions, which are conducive to the development of precision medicine. In addition, according to pretreatment conditions, the cells isolated and purified by the method of the present invention can be used to investigate the cell populations with the different expression of environmental tolerances, such as the degrees of drug resistance, radiation resistance, oxidative stress resistance, toxic chemical resistance, or cell apoptosis. On the other hand, the method of the present invention can be utilized to investigate whether the results of cell sorting caused by different environmental conditions will have differences in gene expression or molecular biological mechanism. Therefore, the present invention has important application value in both clinical medicine and fundamental research.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features, and advantages of this invention will become apparent with reference to the following detailed description and the preferred embodiments taken in conjunction with the accompanying drawings, in which.

DETAILED DESCRIPTION OF THE PREFERRED EMBODIMENT

Figure 1A:
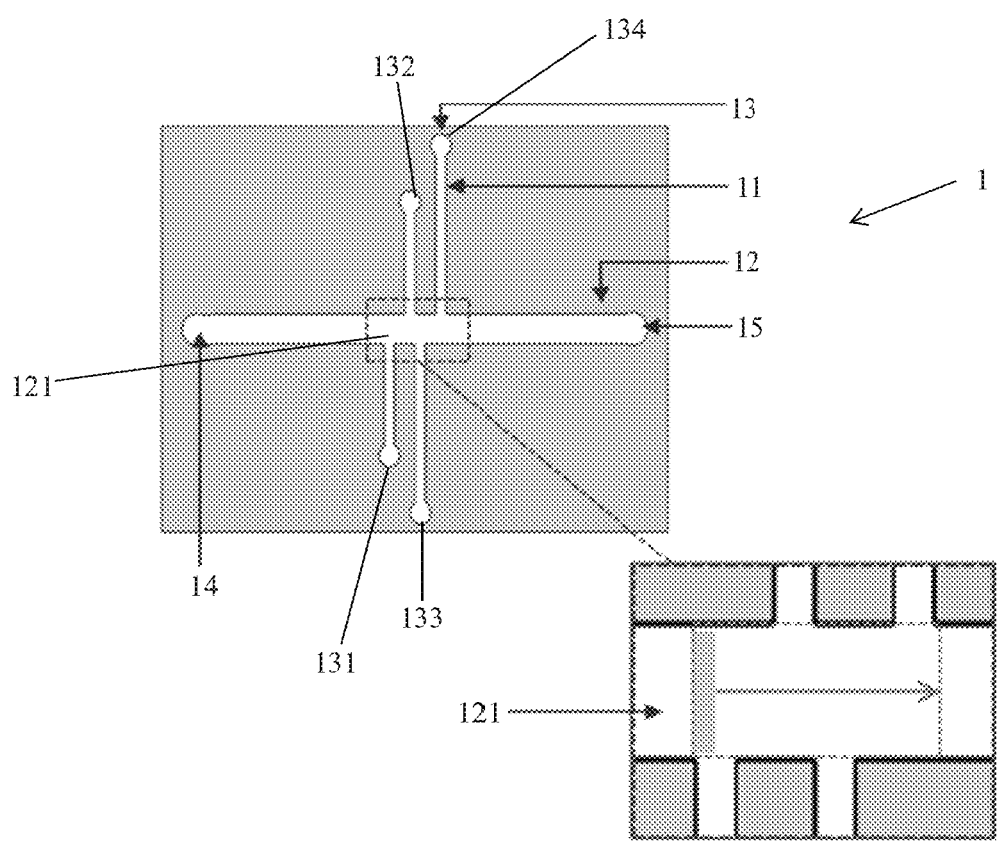
FIG. 1A is a schematic diagram of the optically induced-electrophoresis (ODEP) device of the present invention.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the term "cell viability" refers to the number or percentage of healthy cells (live cells) in a given sample, whereas the cell viability in a single cell is highly associated with the cell membrane integrity, enzyme activity, and redox ability in the cell. The higher the cell viability is expressed as the higher cell membrane integrity and intracellular enzyme activity, making cell physiology status closer to healthy cells (live cell). On the contrary, the lower the cell viability is expressed as the worse cell physiology status which tends to damaged or dead cells.

As used herein, the term "optically-induced dielectrophoresis (ODEP)" refers to a technique using an optoelectronic semiconductor material as a substrate to form a virtual electrode by controlling the light projected below the substrate, inducing a non-uniform electric field in a specific range to polarize and move particles above the substrate (i.e., dielectrophoretic phenomena).

As used herein, the term "optically-induced dielectrophoresis force" means that when a particle is present in a non-uniform electric field generated by light induction, a particle is polarized by a non-uniform electric field and generates an induced electric dipole. The dielectrophoresis forces generated on a particle is due to differences in the degree of polarization in the particles and their surrounding suspensions. The optically-induced dielectrophoresis force ($F_{DEP}$) is calculated according to the following equation (I):

$$F_{DEP}=2\pi r^3\varepsilon_0\varepsilon_m Re[f_{CM}]\nabla|E|^2 \qquad (I)$$

wherein r, $\varepsilon_0$, $\varepsilon_m$, $\nabla|E|^2$, and $Re[f_{CM}]$ denote the cellular radius, vacuum permittivity, relative permittivity of the surrounding solution, gradient of the applied electrical field squared, and real part of the Clausius-Mossotti factor ($f_{CM}$), respectively.

As used herein, the term "light image" means any pattern of light projected by optical equipment (e.g., a projector and laser). In the ODEP system, the light image is directly projected onto the optoelectronic semiconductor material, and its intensity must induce a stable non-uniform electric field to facilitate the generation of ODEP forces.

As used herein, the term "laminar flow" refers to the phenomenon of parallel movement between fluids when the flow channel size is confined to a micron order (i.e., a microchannel).

Example 1

Design of ODEP Device for Isolation and Purification of Cells with Various Degrees of Viability The ODEP device of the present invention is designed to screen, isolate and purify cells with various degrees of viability by utilizing the techniques of ODEP-based cell manipulation in a microfluidic system. The layout of the ODEP device is illustrated in FIG. 1A. FIG. 1A is a schematic diagram of the ODEP device of the present invention. As shown in FIG. 1A, the ODEP device 1 comprises four side microchannels 11, a main microchannel 12, and four target collection tanks 13 (including a first target collection tank 131, a second target collection tank 132, a third target collection tank 133, and a fourth target collection tank 134), a sample loading tank 14, and a waste discharge tank 15. Each of the target collection tanks 13 is disposed at the end of each of the side microchannels 11. The sample loading tank 14 and the waste discharge tank 15 are respectively disposed at opposite ends of the main microchannel 12. The main microchannel 12 has a length of 20 mm, a width of 1.4 mm and a height of 50 μm. The side micro flow channel of the first target collection tank 131 and the second target collection tank 132 has a length of 5.0 mm, a width of 415 μm, and a height of 50 μm. The side micro flow channel of the third target collection tank 133 and the fourth target collection tank 134 has a length of 7.5 mm, a width of 415 μm, and a height of 50 μm. The main microchannel 12 is used for cell suspension, sample transportation, and cell sorting. The side microchannels 11 are designed for collection of the isolated cells. The main microchannel 12 defines a cell isolation zone 121 for performing an ODEP-based cell manipulation. The cell isolation zone 121 has a length of 2.6 mm, a width of 1.4 mm, and a height of 50 μm. The sample loading tank 14 is used to load the fresh cell suspension samples, and the waste discharge tank 15 is used to collect the waste cell suspension samples.

Figure 1B:
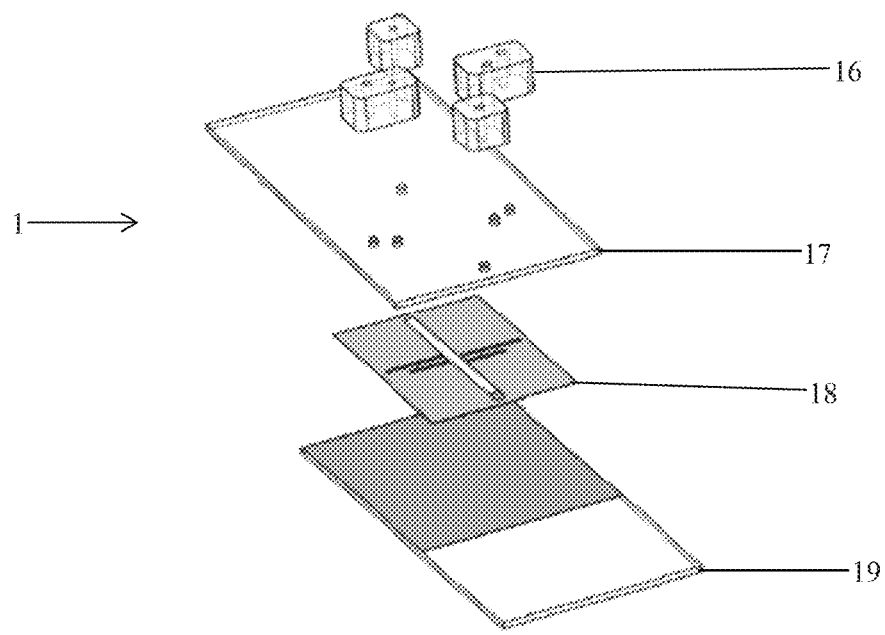
FIG. 1B is an assembly diagram of the ODEP device of the present invention.

FIG. 1B is an assembly diagram of the ODEP device 1 of the present invention. As shown in FIG. 1B, the ODEP device 1 comprises a top fabricated polydimethylsiloxane (PDMS) substrate 16, a first indium-tin-oxide (ITO) glass substrate 17, double-sided adhesive tape with microfabricated microchannels 18 (including the main microchannel 12 and the side microchannels 11; thickness: 50 μm), and a bottom second ITO glass substrate 19 with a coating layer of photoconductive material (encompassing a 20-nm-thick n-type hydrogenated amorphous silicon layer and a 500-nm-thick hydrogenated amorphous silicon layer). The target collection tank 13, the sample loading tank 14, and the waste discharge tank 15 are respectively located at six through-holes on the PDMS substrate 16 and the first ITO glass substrate 17, and the six through-holes are connected directly with the microfabricated microchannels 18.

The sample is injected and removed in the following manner: a suction-type first syringe pump is connected to the waste discharge tank 15 through a connecting conduit, and the cell suspension sample is injected into a PDMS hole of the sample loading tank 14, followed by activating the suction-type first syringe pump to inject the cell suspension sample from the sample loading tank 14 into the cell isolation zone 121 of the main microchannel 12. After the target cells are collected to the side microchannels 11, the target collection tanks 13 are connected to a second syringe pump through a connecting tube, and the second syringe pump is activated to take out the target cells from the side microchannels 11.

The microfabrication and experimental setup of the ODEP device 1 of the present invention are as follows: the overall fabrication process is based on computer-numerical-controlled (CNC) machining, a metal mold-punching fabrication process, PDMS replica molding, a thin-film technology using sputtering and high-density plasma chemical vapor deposition (HDPCVD), and a plasma oxidation-aided bonding process. Briefly, the PDMS substrate 16 was fabricated by a combination of CNC machining and PDMS replica molding. For preparation of the first ITO glass substrate 17, the six through-holes were mechanically drilled in ITO glass (7 Ω, 0.7 mm; Ritek, Taiwan) using a drill (rotational speed: 26,000 rpm). For the microfabricated microchannels 18, a custom-made metal mold was used to create the hollow structure of the microfabricated microchannels 18 in double-sided adhesive tape (L298, Sun-yieh, Taiwan) through manual punch operation. For the second ITO glass substrate 19, a 70 nm-thick ITO layer was first sputtered onto cleaned glass, followed by a thermal annealing process (240° C., 60 minutes). A 20-nm-thick n-type hydrogenated amorphous silicon (n-type a-Si:H) layer was deposited onto the ITO glass through a HDPCVD process. Next, a 500-nm-thick hydrogenated amorphous silicon (a-Si:H) layer was deposited onto the treated ITO glass through the HDPCVD process. Subsequently, the PDMS substrate 16 was bonded with the first ITO glass substrate 17 via $O_2$ plasma surface treatment. The first ITO glass substrate 17 bonded with the PDMS substrate 16 was followed by assembled with the second ITO glass substrate 19 through the microfabricated microchannels 18 with the double-sided adhesive tape.

Figure 1C:
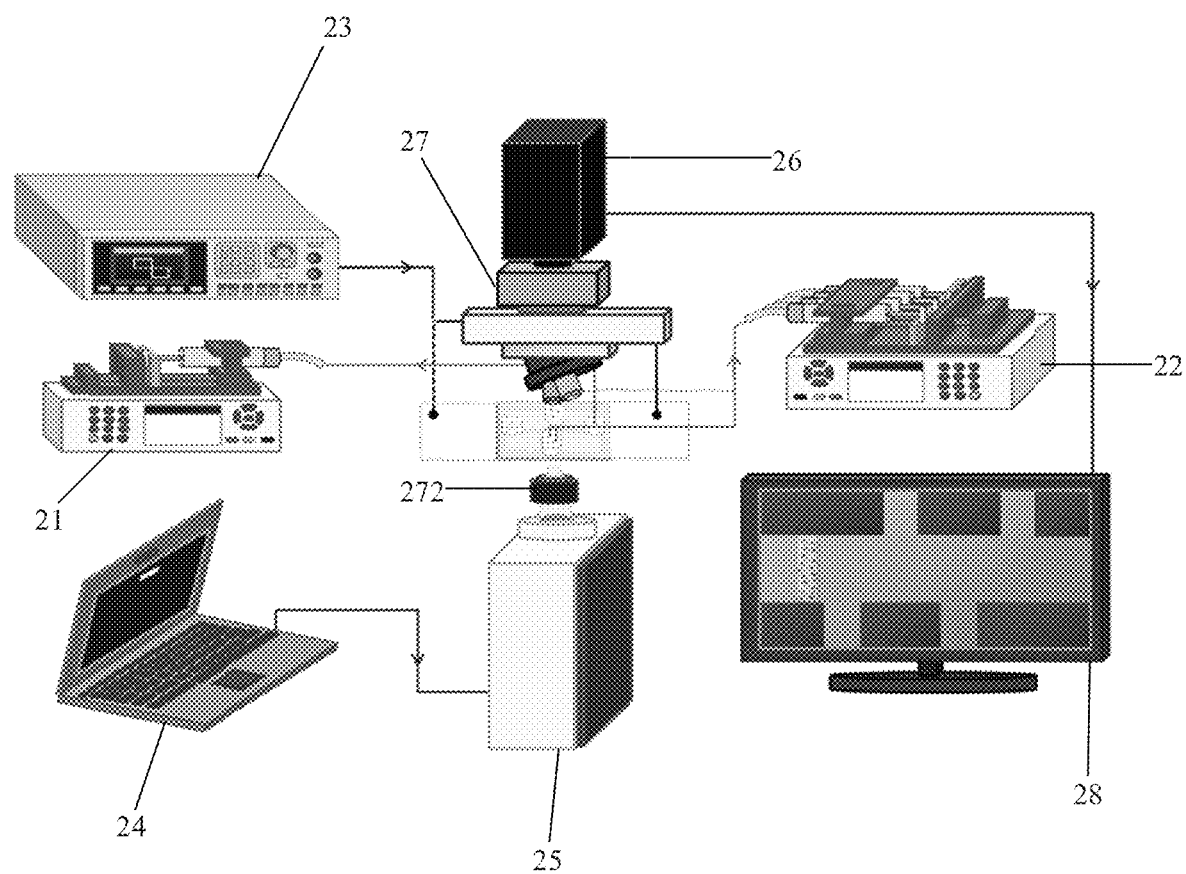
FIG. 1C is a schematic diagram showing the installation of the ODEP device of the present invention.
Figure 1D:
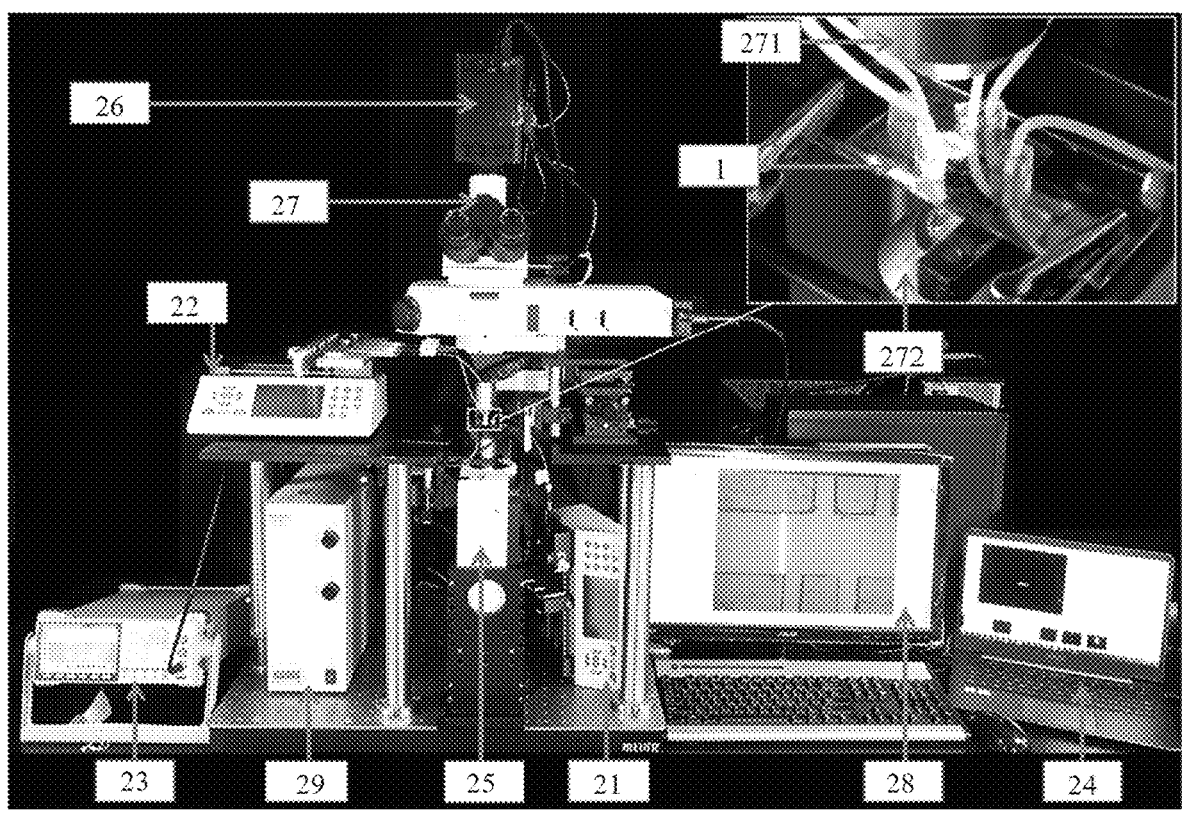
FIG. 1D is an entity diagram showing the installation of the ODEP device of the present invention.

FIG. 1C is a schematic diagram showing the installation of the ODEP device 1 of the present invention. FIG. 1D is an entity diagram showing the installation of the ODEP device 1 of the present invention. During operation, the ODEP device 1 was integrated into a chip, the loaded cell suspension sample was transported into the main microchannel 12 via the sample loading tank 14 by using a suction-type first syringe pump 21. A suction-type second syringe pump 22 was utilized to harvest the cells isolated and temporarily stored in the target collection tanks 13. A function generator 23 was used to apply an alternating current (AC) between the first ITO glass substrate 17 and the second ITO glass substrate 19. A commercial digital projector 25 (PLC-XU350, SANYO, Japan) coupled with a computer 24 was used to display light images through a 10× objective lens 272 onto the second ITO glass substrate 19 with a coating layer of photoconductive material to generate ODEP force on the manipulated cells. In addition, a charge-coupled device 26 (CCD)-equipped fluorescence microscope 27 (Zoom 160, OPTEM, USA; including a 4× objective lens 271) was utilized to observe the manipulation of cells, and the image was displayed on the desktop 28. As for the lamp 29, it is used to generate a background light source for microscopic observation of the cells, so that the movement path of the cells and the fluorescent staining can be clearly observed during the operation. Besides, the intensity of the microscope background light source projected by the lamp 29 does not affect the cells manipulated by the light images projected by the projector.

Example 2

Figure 2A:
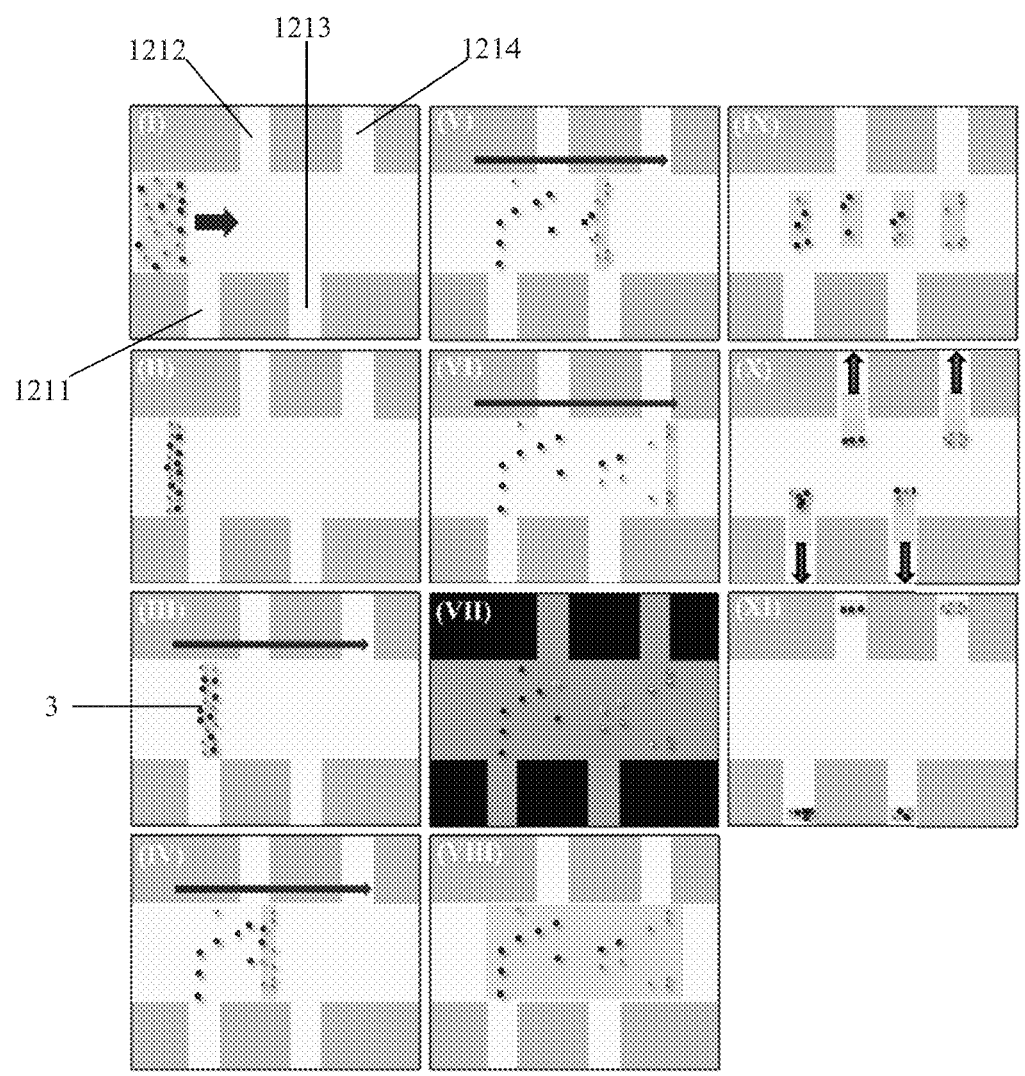
FIG. 2A is a flow chart showing the operation of the method of the present invention for screening, isolating and purifying an analyte, in which Dx5 represents MES-SA cells with anti-cancer drug resistance; calcein-AM represents a fluorescent dye that can identify live cells; DiB represents a cytoplasmic membrane labelling dye; EthD-1 represents a fluorescent dye that can identify dead cells.
Figure 2B:
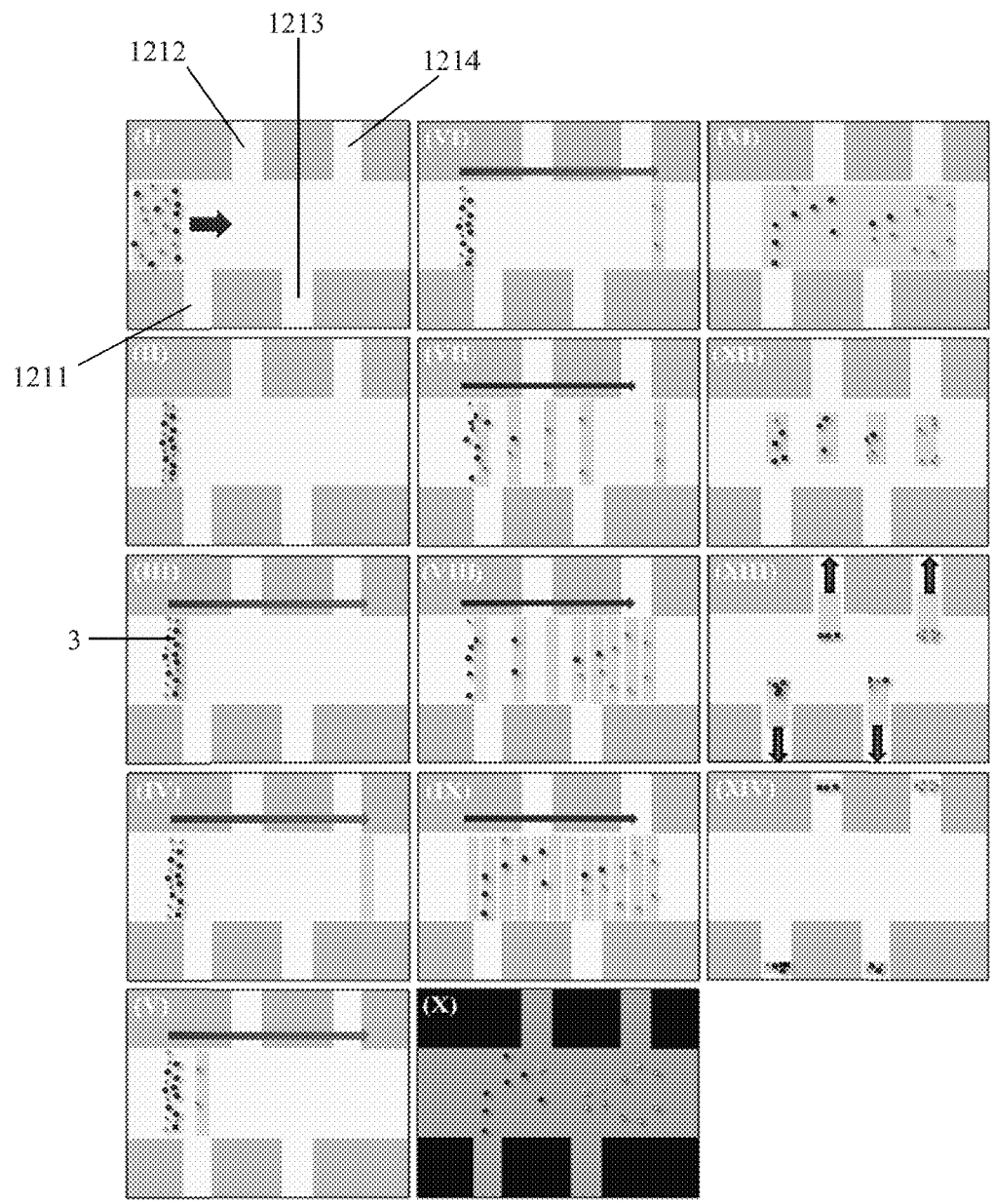
FIG. 2B is another flow chart showing the operation of the method of the present invention for screening, isolating and purifying an analyte.

The Operation Scheme for Screening Various Degrees of Cell Viability, and Isolating and Purifying Cells with Various Degrees of Cell Viability In the present embodiment, the method of the present invention is performed by using the ODEP device, and the operation procedures are shown in FIGS. 2A and 2B. Briefly, the anti-cancer-drug (i.e., doxorubicin)-treated human uterine sarcoma cells (MES-SA cells; obtained from the Bioresource Collection and Research Center (BCRC) of Food Industry Research and Development Institute (FIRDI)) were stained with fluorescent dyes to identify their live or dead status. The prepared cell suspension sample was then loaded into the ODEP device. Thereafter, the light images projected by the projector and the ODEP force were used to gather the cells to the start line of the cell isolation zone (FIG. 2 A (I)-(II)). FIGS. 2A (I) and (II) show a dynamic light image which is slowly contracted from a large square into a light bar, making dispersed cells gathered to the start line. In the subsequent steps, a moving rectangular light bar (i.e., the ODEP force light image module 3, that is, FIG. 2A (III) to (VI), comprising at least one first moving light bar, and the moving velocity of the at least one first moving light bar is a variable speed) (L: 1.3 mm, W: 100 μm) with 12 different moving velocities (starting velocity: 16.7 μm $s^{-1}$; increment: 16.7 μm $s^{-1}$ per 217 μm of moving distance; terminal velocity: 200 μm $s^{-1}$) was designed to manipulate the cells and spread them across the cell isolation zone, as illustrated in FIG. 2A (III)-(VI). Observation via fluorescence microscopy was subsequently performed to evaluate the cell sorting performance of the previous operation procedure (FIG. 2A (VII)). This was soon followed by isolating the cells distributed in the four individual subzones of the cell isolation zone into the four corresponding side microchannels. During operation, a light image with a large area (L: 2.6 , W: 1.3 mm) was used first to illuminate the cell isolation zone (FIG. 2A (VIII)), soon followed by splitting of the light image into four smaller rectangular light images (L: 415.8 μm, W: 222.8 μm) located at the front of the entrances of the four side microchannels (FIG. 2A (IX)). The four rectangular light images were then moved to manipulate the cells located within the four subzones (including the subzone 1211 (subzone 1), the subzone 1212 (subzone 2) the subzone 1213 (subzone 3) and the subzone 1214 (subzone 4)) and delivered them via the ODEP force into the four corresponding side microchannels, as shown in FIG. 2A (X)-(XI).

In the operation model of FIG. 2B, since the cell velocity of the real sample is not known by experiment, it differs from FIG. 2A that the velocities of the moving rectangular light bar (i.e., the ODEP force light image module 3, that is, FIG. 2B (III) to (IX), comprising a plurality of second moving light bars, the moving velocity of the light image among the plurality of second moving light bars is different, and the moving velocity of the light image is a constant speed) that can manipulate cells are unknown. The cell staining, loading, and manipulation (FIGS. 2B (I) and (II)) processes before the subsequent cell sorting process were the same as those described earlier and shown in FIGS. 2A (I) and (II). In the following steps for sorting and separation of cells, the key difference from the previous model in FIG. 2A was use of a moving rectangular light bar with a wide velocity range (from high to low velocity) to screen the cell sample. During operation, a rectangular light bar with a high moving velocity (e.g., 500 μm $s^{-1}$) was first used to manipulate the cells (i.e., screen the cells through the ODEP force to drive cells; FIG. 2B (III) and (IV)). If no cell was manipulated (FIG. 2B (IV)), the moving velocity used for the next round of screening was gradually decreased in a set decrement of 25 μm s$^{-1}$. Once more than two cells were able to be manipulated by the moving light bar at a particular moving velocity (FIG. 2B (V)), the moving light bar was set to stop at the terminal of the defined cell isolation zone, as shown in FIG. 2B (VI). In the operation model of FIG. 2B, the operation of the light image is decremented from high velocity to low velocity. When the moving velocity of the light image is higher than the velocity at which the cells can be manipulated, no cells are moved by the light image. However, in FIG. 2B (V) to (VI), once the moving velocity of the light image is sufficient to manipulate at least two cells or more, the velocity is defined as the maximum manipulating velocity of the cells in this model, and the velocity of subsequent 11 moving light bars is defined by the maximum manipulating velocity of the cells. Therefore, in FIG. 2B (VI), the reason for displaying two cells on the moving light bar is to indicate that the maximum cell manipulating velocity of this model is capable of simultaneously manipulating at least two cells. On the other hand, there is no cell in the moving light bar in FIG. 2B (IV) because the velocity of the moving light image is greater than the velocity of cells which can be manipulated. After that, another 11 moving light bars with a series of gradient velocities defined as the maximum manipulating velocity according to FIG. 2B (VI) were designed to screen the cells within the cell isolation zone, as illustrated in FIG. 2B (VII)-(IX). Soon after this process, these 11 moving light bars were designed to align and stop in the cell isolation zone, as illustrated in FIG. 2B (IX). The following steps were the same as the procedures described in FIG. 2A. Briefly, fluorescence microscopy observation was subsequently performed to evaluate the cell sorting effect of the previous operation procedure (FIG. 2B (X)). This was soon followed by isolation of the cells distributed in the four individual subzones (including the subzone 1211 (subzone 1), the subzone 1212 (subzone 2) the subzone 1213 (subzone 3) and the subzone 1214 (subzone 4)) of the cell isolation zone in the four corresponding side microchannels (FIG. 2B (XI)-(XIV)).

The method of the present invention is used to screen various degrees of cell viability and to isolate and purify cells with various degrees of cell viability. The key working mechanism is the ODEP force generated on the cells, which would vary with the conductivity of the cytoplasm. Based on this, the moving rectangular light bar with 12 different moving velocities was designed to manipulate the cells for screening and isolating cells in the cell isolation zone depending on the degrees of cell viability, as shown in FIG. 2A.

Example 3

Evaluation of Effect of Anti-Cancer Drug (Doxorubicin) on Percentage of Live Cells, Cell Viability, and Cell Size of Cancer Cells with and without Anti-Cancer Drug Resistance In the present embodiment, cancer cell lines with (MES-SA/Dx5 cells; abbreviated as "Dx5" from the BCRC of Food Industry Research and Development Institute (FIRDI), Taiwan) and without (MES-SA cells from the BCRC of FIRDI) anti-cancer drug resistance were separately treated with various concentrations (0, 2.5, 5.0, 7.5, 10.0, 12.5, 15.0 μg ml$^{-1}$) of doxorubicin (doxorubicin hydrochloride; Enzo Life Sciences, CH) for 48 hours. The percentage of live cells was then evaluated by a combination of fluorescent dye staining and microscopic observation. Briefly, the drug-treated Dx5 cells were stained with the DiB cytoplasmic membrane labelling dye (Biotium, CA USA) and EthD-1 fluorescent dye (ethidium homodimer-1; Thermo Fisher Scientific, MA USA) to identify the living (blue staining), and dead (red staining) Dx5 cells, respectively. The drug-treated MES-SA cells were stained with Calcein-AM and EthD-1 fluorescent dyes (LIVE/DEAD1 Viability/Cytotoxicity Kit L-3224; Thermo Fisher Scientific, MA USA) to identify the living (green staining) and dead (red staining) cells, respectively. All the assays were performed according to the manufacturer's instructions. This was followed by microscopic observation using a fluorescence microscope (Zoom 160, OPTEM, USA). The overall viability of the cancer cells was then evaluated by determining the number of live cells relative to that of whole cells.

Cell viability was also evaluated by assaying the intercellular dehydrogenase activity of cells using the commonly used MTT (thiazolyl blue tetrazolium bromide; Sigma Aldrich, MO USA) assay. Briefly, the cancer cells (i.e., MES-SA and Dx5 cells) were separately treated with doxorubicin as mentioned above. The drug-treated cancer cells were then assayed for viability (%) based on the manufacturer's instructions for the MTT assay kit. The results of the present embodiment are shown in FIGS. 3A and 3B.

Figure 3A:
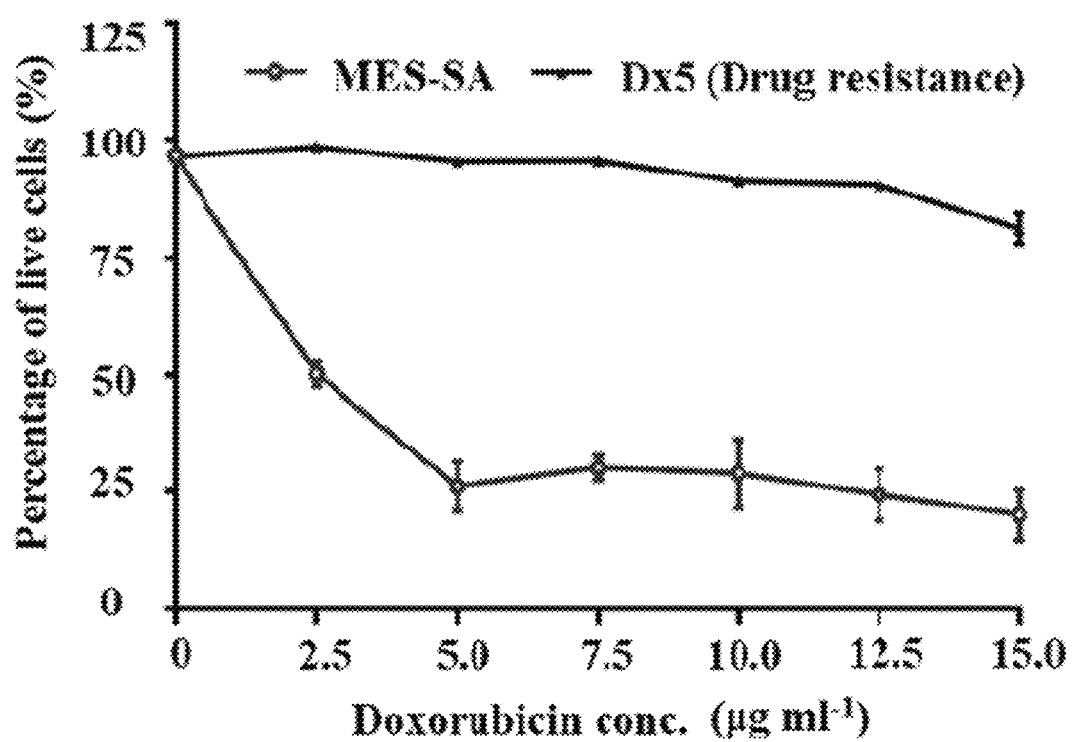
FIG. 3A is a schematic diagram showing the ratio of live cells in cancer cells with and without anti-cancer drug resistance after the anti-cancer drug (doxorubicin) is administrated, in which live and dead cells are distinguished by fluorescent dyes (i.e., calcein-AM and EthD-1).
Figure 3B:
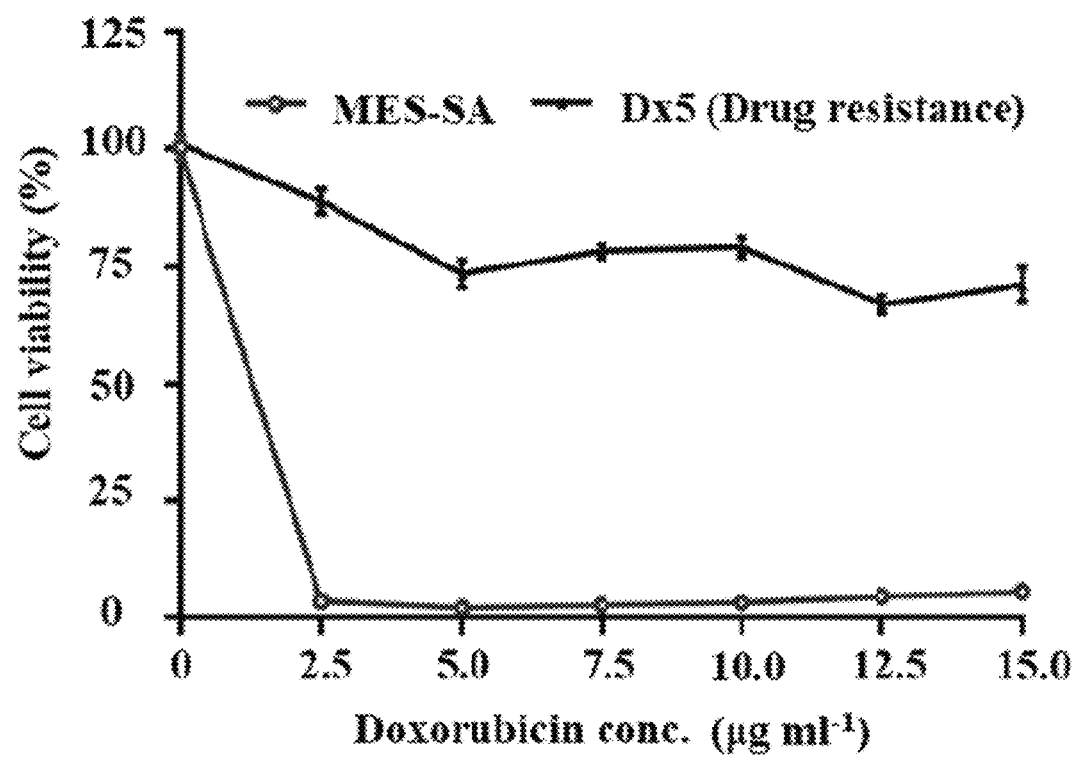
FIG. 3B is a schematic diagram showing the cell viability of cancer cells with and without anti-cancer drug resistance after the anti-cancer drug (doxorubicin) is administrated, in which the cell viability is determined by the value of MTT assay which is utilized to measure the redox ability of intracellular mitochondria.

FIG. 3A is a schematic diagram showing the ratio of live cells in cancer cells with and without anti-cancer drug resistance after anti-cancer drug (doxorubicin) treatment. FIG. 3B is a schematic diagram showing the cell viability of cancer cells with and without anti-cancer drug resistance after the anti-cancer drug (doxorubicin) treatment. As shown in FIG. 3A, for the Dx5 cells, the percentage of live cells slightly decreased with an increase in drug concentration. Overall, for the drug-treated Dx5 cells, the percentage of live cells remained within the range of 81.1% to 98.5% within the experimental conditions explored. Conversely, for the MES-SA cells, the percentage of live cells dramatically decreased when the drug concentration was increased from 0 to 5.0 μg ml$^{-1}$, after which the percentage of live cells showed no significant difference (p>0.05). Overall, for the drug-treated MES-SA cells, the percentage range of live cells was in the range of 20.0% to 50.3%. As shown in FIG. 3B, the cell viability (%) reached nearly 0% when the MES-SA cells were treated with various concentrations of doxorubicin. Conversely, for Dx5 cells, the cell viability significantly declined when the drug concentration was increased from 0 to 5.0 μg ml$^{-1}$, after which the cell viability exhibited no significant difference (p>0.05) when the drug concentration was further increased from 5.0 to 10.0 μg ml$^{-1}$. Based on the above evaluations, the 5.0 μg ml$^{-1}$ doxorubicin concentration was selected for the following experiments because the live and dead status difference [fluorescent dye staining (percentage of live cells): 95.5% and 26.1%; MTT assay (cell viability): 73.5% and 2.2% for the Dx5 and MES-SA cells, respectively] of the two cancer cell lines tested was significant.

Figure 3C:
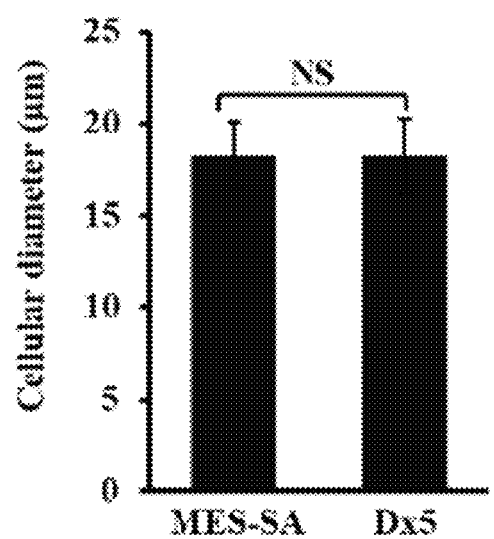
FIG. 3C is a schematic diagram showing cell sizes of Dx5 cells and MES-SA cells without drug treatment, in which NS indicates no significant difference.
Figure 3D:
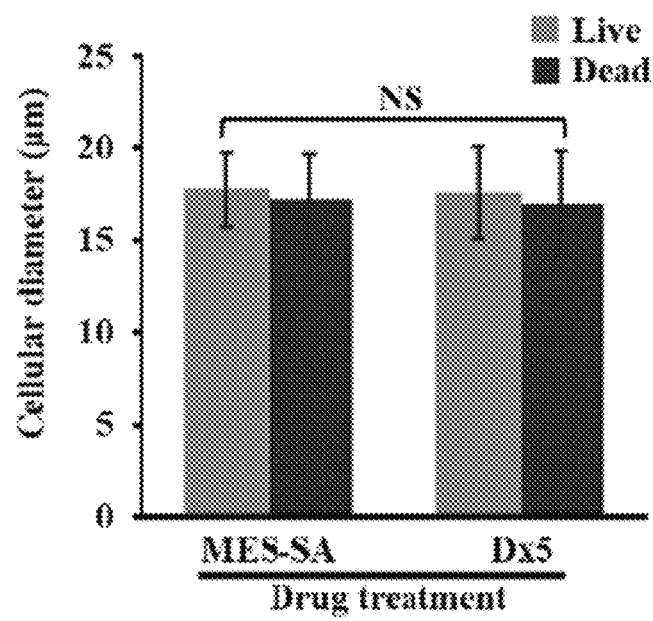
FIG. 3D is a schematic diagram showing the effect of the anti-cancer drug (doxorubicin) on the cell size of cancer cells with and without anti-cancer drug resistance, in which NS indicates no significant difference.

To evaluate whether the size of the cells could interfere with the cell sorting mechanism, the size differences of the two drug-treated (5.0 μg ml$^{-1}$ doxorubicin for 48 hours) cancer cell lines (i.e., MES-SA and Dx5 cells) were assessed microscopically. The results are shown in FIGS. 3C and 3D. FIG. 3C is a schematic diagram showing cell sizes of Dx5 cells and MES-SA cells without drug treatment. FIG. 3D is a schematic diagram showing the effect of the anti-cancer drug (doxorubicin) on the cell size of cancer cells with and without anti-cancer drug resistance. As shown in FIG. 3C, the mean diameters of the MES-SA and Dx5 cells without drug treatment were 18.2±1.9 and 18.2±2.0 µm, respectively, indicating no significant difference (p>0.05) between them. As shown in FIG. 3D, after the cells were treated with drug, the sizes of the live and dead MES-SA and Dx5 cells also exhibited no significant difference (p>0.05) (cellular diameter range: 17.0-17.7 µm). According to the results, the influence of cell size on the proposed mechanism for sorting cells based on their degree of viability could be reasonably ruled out.

Example 4

Optimal ODEP Operating Conditions for Sorting and Isolation of Cells with Various Degrees of Cell Viability To demonstrate the feasibility of the method of the present invention, the optimal operation conditions (including the electric conditions for ODEP and the velocity profile of the moving rectangular light bar) were experimentally determined. For the electric conditions, the magnitude and frequency of the ODEP were set at 10 V and 2 MHz, which can reduce cell aggregation and accelerate cell sorting and isolation, as shown in FIG. 2A. In addition, the ODEP manipulation force, a net force between the ODEP force and friction force, generated on the manipulated cells (i.e., the live and dead cancer cells with and without drug resistance) was then experimentally evaluated. Briefly, in a steady state, the ODEP manipulation force on a cell is balanced by the viscous drag of the surrounding fluid. Therefore, the hydrodynamic drag force of a moving cell was normally used to evaluate the net ODEP manipulation force of a cell (according to Stokes' law (equation II), described as the drag force (F) exerted on a spherical particle under a continuous flow condition):

$$F = 6\pi r \eta v \qquad (II)$$

where r, η, and v denote the radius of a cell, the viscosity of the fluid, and the maximum velocity of a cell, respectively.

Figure 4:
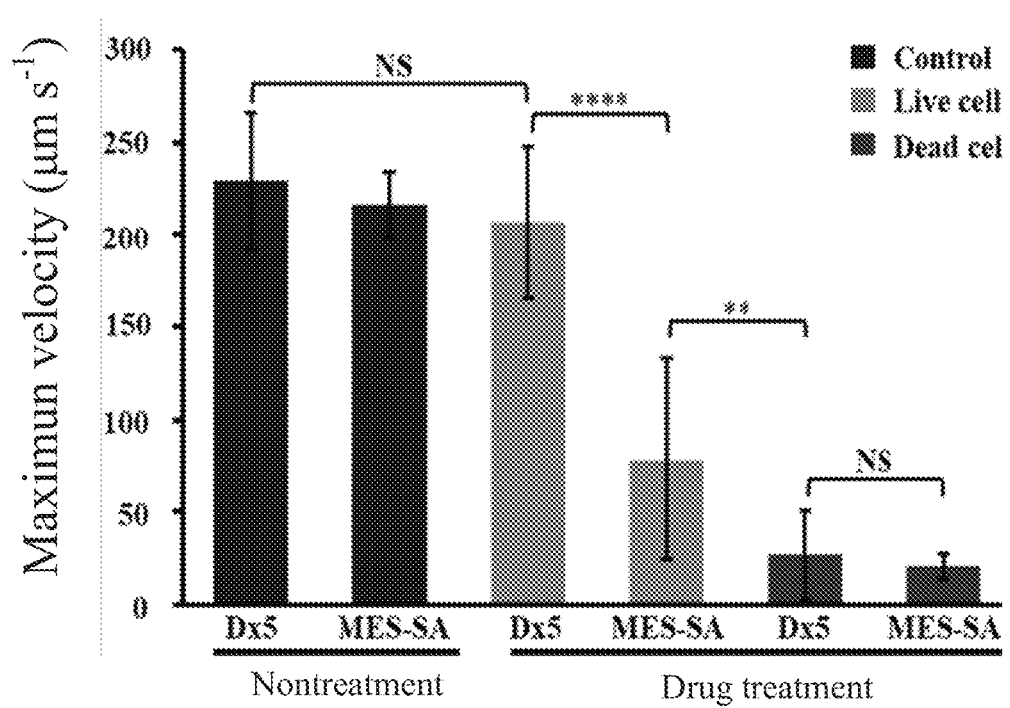
FIG. 4 is a schematic diagram showing the maximum velocity of the moving light bar that can manipulate MES-SA cells and Dx5 cells before and after treatment with anti-cancer drugs, in which NS indicates no significant difference;  indicates $p<0.01$; ** indicates $p<0.0001$.

Therefore, according to Stokes' law, the ODEP manipulation force generated on the cells can then be experimentally evaluated through measurements of the maximum velocity of a moving light bar that can manipulate these cells (i.e., live and dead MES-SA cells and Dx5 cells). FIG. 4 is a schematic diagram showing the maximum velocity of the moving light bar that can manipulate MES-SA cells and Dx5 cells before and after treatment with anti-cancer drugs. As shown in FIG. 4, the maximum velocities of the moving light bar that can manipulate the live MES-SA and Dx5 cells before drug treatments were 215.8±18.0 and 229.2±37.2 µm s$^{-1}$, respectively, indicating no significant difference (p>0.05) between them. This finding was consistent with the previous result revealing that the size of the MES-SA and Dx5 cells before drug treatment was not significantly different (FIG. 3C), which is an important factor determining the generation of ODEP force on a cell (equation (I)). After the live MES-SA and Dx5 cells were treated with 5.0 µg ml$^{-1}$ doxorubicin for 48 hours, the maximum velocity of the moving light bar that can manipulate live Dx5 cells was measured to be 206.7±41.0 µm s$^{-1}$, showing no significant difference (p>0.05) with that of the MES-SA and Dx5 cells before drug treatment. However, for the drug-treated live MES-SA cells, the abovementioned velocity (78.3±54.4 µm s$^{-1}$) decreased significantly in comparison with that for drug-treated live Dx5 cells (p<0.05). This phenomenon was not caused by the size of the cells because the drug-treated live MES-SA and Dx5 cells showed no significant difference in cell size (FIG. 3D). Therefore, the difference in the velocities of MES-SA cells and Dx5 cells after drug treatment is caused by the difference in cell viability.

Furthermore, regarding the drug-treated dead MES-SA and Dx5 cells, FIG. 4 reveals that the maximum velocities of the moving light bar that could manipulate these cells (i.e., 20.6±6.8 and 26.9±24.2 µm s$^{-1}$, respectively) were not significantly different (p>0.05), and these velocities were found to be significantly lower (p<0.05) than that for the live MES-SA cells. This finding could be explained by the abovementioned fact in which the level of cell damage raised that therefore leads to an increase in ion loss from the cell cytoplasm of a damaged cell, and the maximum velocity measured was decreased. Based on the results, it was found that a moving light bar with different velocities (i.e., the ODEP force light image module having a controllable velocity) could be used to manipulate and thus sort the drug-treated live Dx5 cells (206.7±41.0 µm s$^{-1}$), live MES-SA cells (78.3±54.4 µm s$^{-1}$), and the dead cells (20.6±6.8 to 26.9±24.2 µm s$^{-1}$) owing to their differences in cell viability level. According to this information, a moving rectangular light bar with 12 different moving velocities (starting velocity: 16.7 µm s$^{-1}$; increment: 16.7 µm s$^{-1}$ per 217 µm of moving distance; terminal velocity: 200 µm s$^{-1}$) was designed to sort, isolate and purify the drug-treated cancer cells as described in FIG. 2A.

Example 5

Feasibility Evaluation of the Method of the Present Invention and Analysis of Drug Resistance Gene Expression of Cells Sorted, Isolated and Purified by the Method of the Present Invention To demonstrate the feasibility of the method of the present invention, the operation procedure shown in FIG. 2A was carried out. In this example, MES-SA and Dx5 cells were treated with 5.0 µg ml$^{-1}$ doxorubicin for 48 hours. After that, equal amounts of the drug-treated MES-SA and Dx5 cells were well mixed, and then the proposed method in FIG. 2A was applied for cell sorting, isolation and purification. The percentage of dead cells (i.e., EthD-1 fluorescent dye-positive cells) in the 12 different moving velocities was evaluated microscopically. The result is shown in FIG. 5.

Figure 5:
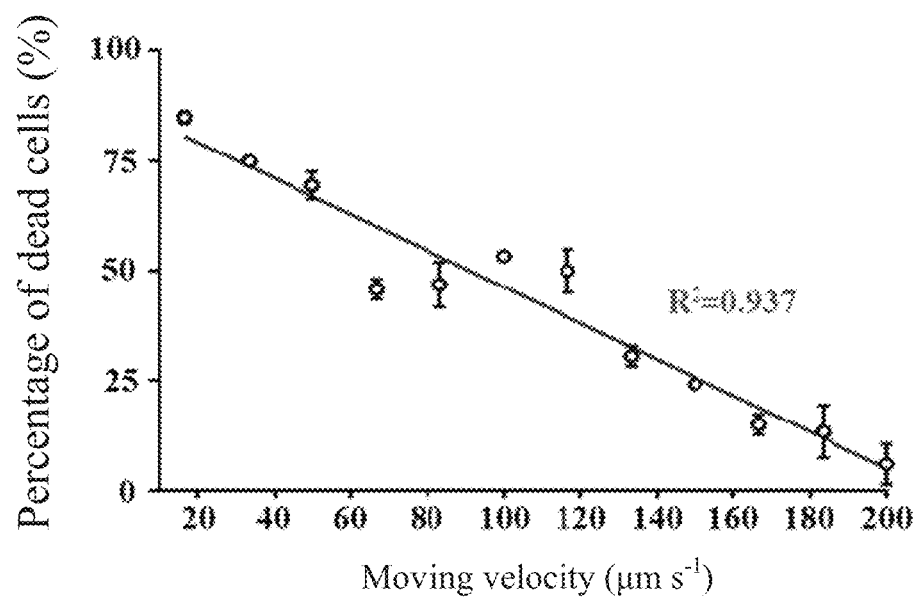
FIG. 5 is a schematic diagram showing the percentage of dead cells (i.e., EthD-1 fluorescent dye-positive cells) in a moving rectangular light bar with 12 different moving velocities.

FIG. 5 is a schematic diagram showing the percentage of dead cells (i.e., EthD-1 fluorescent dye-positive cells) manipulated by a moving rectangular light bar with 12 different moving velocities. As shown in FIG. 5, the percentage of dead cells decreased from the low to high velocity (i.e., velocity 16.7 to 200 µm s$^{-1}$), in which the percentage of dead cells reached 6.1% when the velocity was 200 µm s$^{-1}$. Moreover, in FIG. 5, the moving velocity and the percentage of dead cells showed good correlation ($R^2$: 0.937), which overall demonstrated that the method of the present invention was capable of sorting and separating cells based on their degrees of cell viability.

To evaluate drug resistant natures in the distribution of the drug-treated cancer cells in the four subzones of the cell isolation zone, the drug-treated cancer cells sorted, isolated, and then purified via the operation scheme in FIG. 2A or FIG. 2B were harvested for the following multidrug resistance gene expression assays.

In this example, the mRNA levels of a multidrug resistance gene (ATP binding cassette subfamily B member 1, ABCB1) (Hs00184500_m1; Thermo Fisher Scientific, MA USA) and a house-keeping gene (glyceraldehyde-3-phosphate dehydrogenase, GAPDH) were quantified based on the method well known in the art, see Chiu T K et al. (2016), Sci Rep., 6:32851. doi: 10.1038/srep32851. Briefly, RNA was extracted from cells using a PicoPure RNA Isolation Kit (Thermo Fisher Scientific, MA USA). This was followed by reverse transcription using a SuperScript® IV Reverse Transcriptase Kit (Thermo Fisher Scientific, MA USA) and preamplification using a TaqMan® PreAmp Master Mix Kit (Thermo Fisher Scientific, MA USA). The mRNA level was subsequently quantified via using a StepOne™ Real-Time PCR System (Thermo Fisher Scientific, MA USA). The result is shown in FIG. 6A.

Figure 6A:
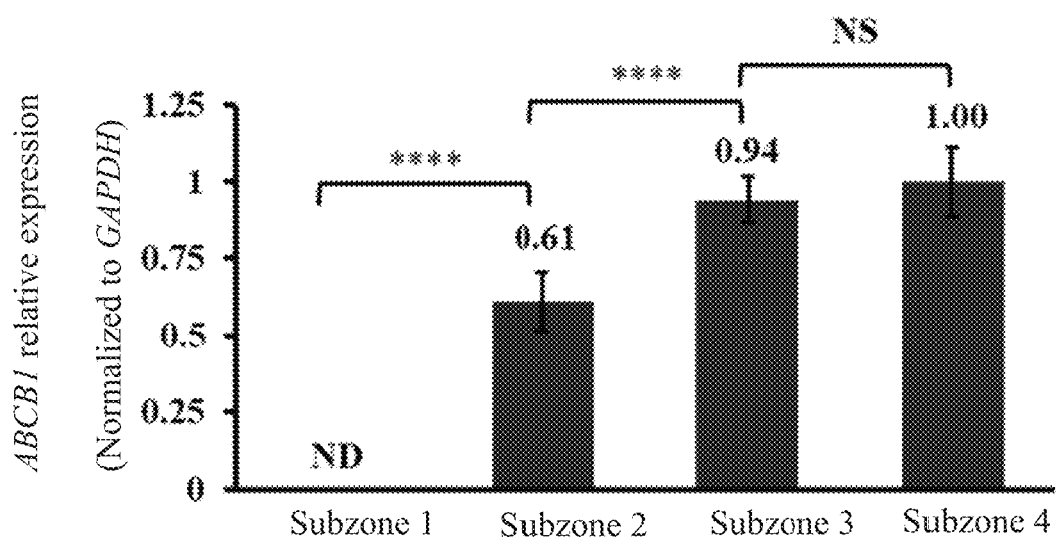
FIG. 6A is a schematic diagram showing the analysis of drug resistant gene expression of cells screened, isolated and purified according to the method of the present invention using the operation model in FIG. 2A, in which ND indicates no detection; NS indicates no significant difference; **** indicates $p<0.0001$.

FIG. 6A is a schematic diagram showing the analysis of drug resistant gene expression of cells screened, isolated and purified according to the method of the present invention using the operation model in FIG. 2A, in which the corresponding locations of subzones 1 to 4 are shown in FIG. 2A. As shown in FIG. 6A, the ABCB1 gene expression significantly increased from the subzone 1211 (subzone 1; no ABCB1 gene expression was detected) to the subzone 1213 (subzone 3), and the ABCB1 gene expression level in the cells in the subzone 1213 and the subzone 1214 (subzone 4) was not significantly different ($p>0.05$). This result demonstrates that the method of the present invention is indeed useful for screening, isolating and purifying drug-treated cells with various degrees of drug resistance gene expression.

In the operation model of FIG. 2A, the velocity of the moving rectangular light bar used to manipulate the cells is known. The operation procedure shown in FIG. 2B is then performed in this example, that is, the velocities of the moving rectangular light bars for manipulating the cells are unknown, and the drug-treated cancer cells thus screened, isolated and purified are subjected to analysis of multidrug resistance gene expression referring to the aforementioned method. The result is shown in FIG. 6B.

Figure 6B:
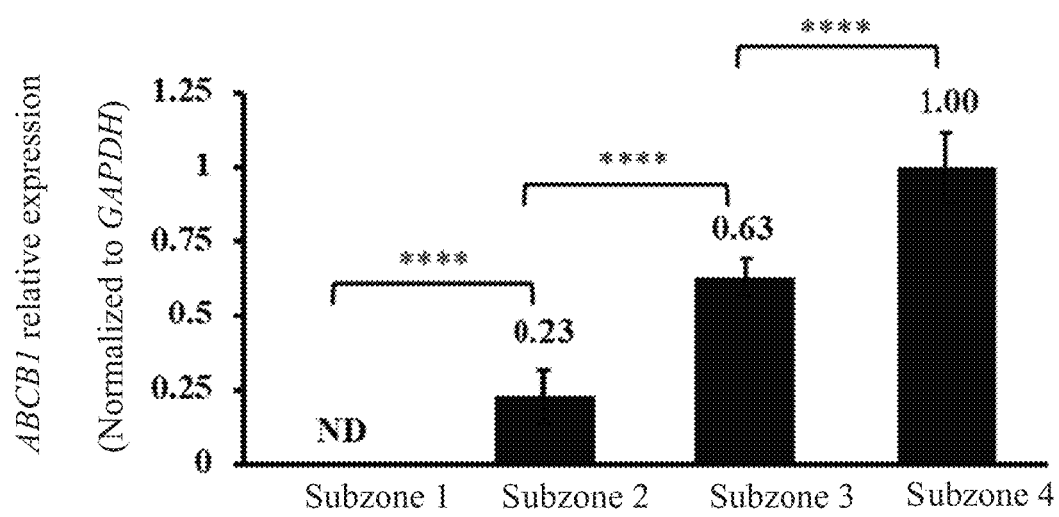
FIG. 6B is another schematic diagram showing the analysis of drug resistant gene expression of cells screened, isolated and purified according to the method of the present invention using the operation model in FIG. 2B, in which ND indicates no detection; **** indicates $p<0.0001$.

FIG. 6B is another schematic diagram showing the analysis of drug resistant gene expression of cells screened, isolated and purified according to the method of the present invention using the operation model in FIG. 2B, in which the corresponding locations of subzones 1 to 4 are shown in FIG. 2B. As shown in FIG. 6B, the ABCB1 gene expression significantly increased from the subzone 1211 (subzone 1; no ABCB1 gene expression was detected) to the subzone 1214 (subzone 4), and the ABCB1 gene expression level in the cells in the subzone 1213 (subzone 3) and the subzone 1214 (subzone 4) was significantly different ($p<0.05$). This result demonstrates that the method of the present invention is indeed useful for screening, isolating and purifying drug-treated cells with various degrees of drug resistance gene expression regardless of whether the velocities of the moving rectangular light bars used to manipulate the cells are known (see FIG. 2A) or unknown (see FIG. 2B).

To further understand the distribution of cells in the four subzones of the cell isolation zone using the operation model in FIG. 2B, a cell sample for testing was prepared by mixing equal amounts of drug-treated and fluorescent dye-stained MES-SA and Dx5 cells. The prepared cell sample was processed using the operation model described in FIG. 2B and observed via fluorescence microscopy to quantify the live and dead Dx5 and MES-SA cells. The result is shown in FIG. 7A.

Figure 7A:
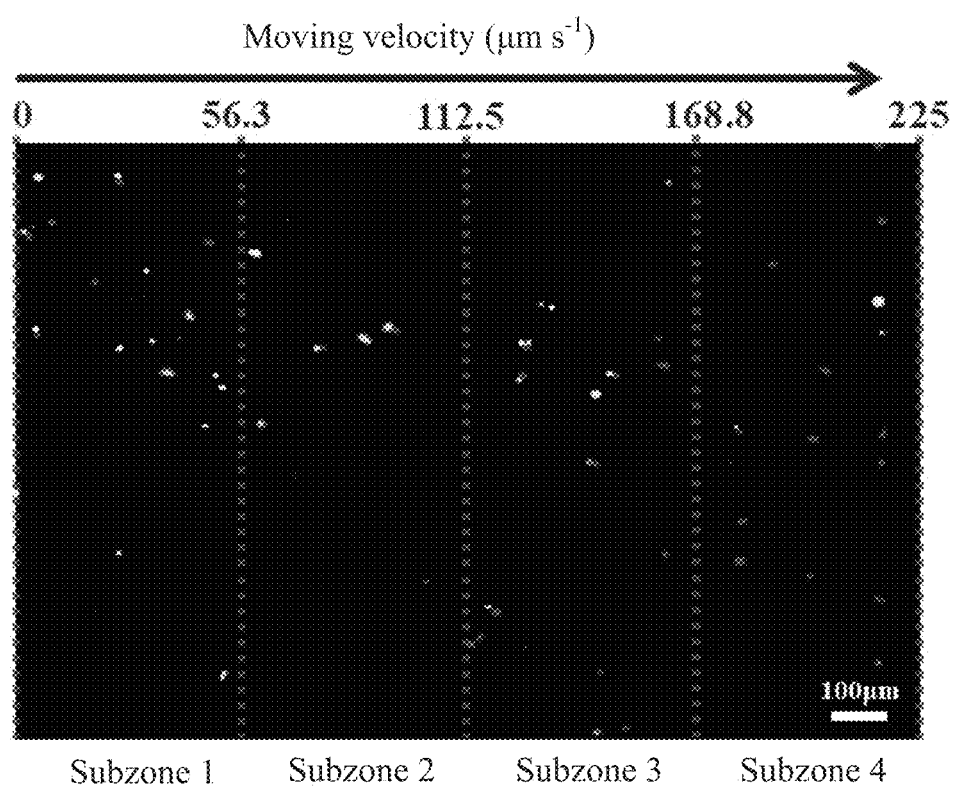
FIG. 7A is an image diagram showing the distribution of cells screened, isolated and purified according to the method of the present invention in a cell isolation zone observed by a fluorescence microscope.

FIG. 7A is an image diagram showing the distribution of cells screened, isolated and purified according to the method of the present invention in a cell isolation zone observed by a fluorescence microscope. As shown in FIG. 7A, the number of live Dx5 cells (blue staining) increased gradually from subzone 1 to subzone 4, whereas the dead cells (red staining) decreased from subzone 1 to subzone 4. To further evaluate the live and dead status of cells and the cell species in this cell distribution, the operation model in FIG. 2B was repeated for 3 times to collect an adequate number of cells from the defined four subzones of the cell isolation zone for subsequent cell counting. The result is shown in FIG. 7B.

Figure 7B:
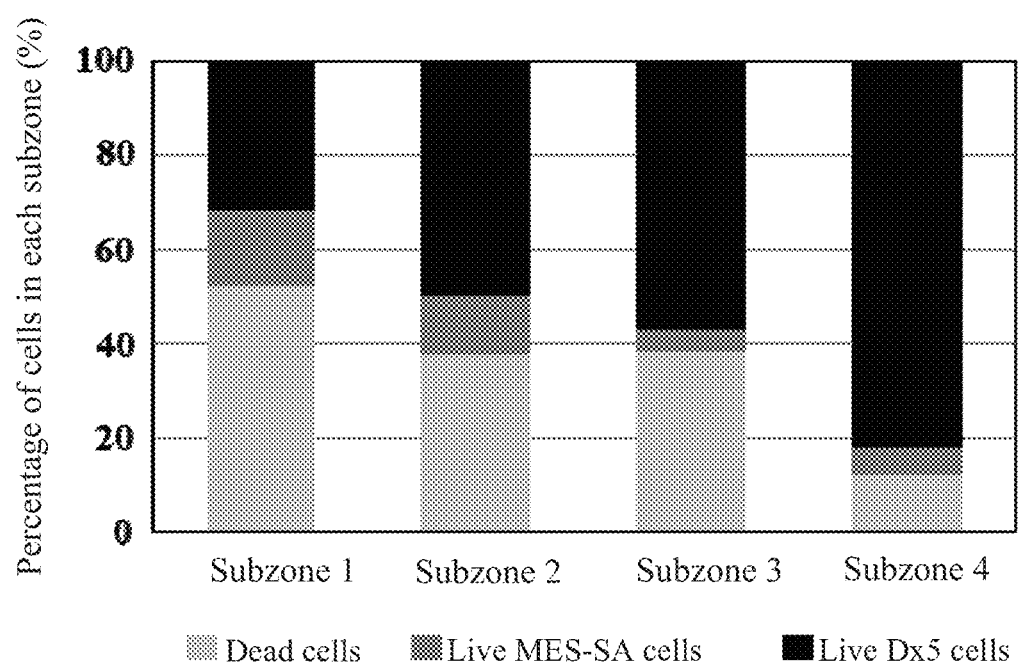
FIG. 7B is a schematic diagram showing the distribution (percentage) of cells (i.e., MES-SA cells and Dx5 cells) screened, isolated and purified according to the method of the present invention in four subzones of the cell isolation zone.

FIG. 7B is a schematic diagram showing the distribution (percentage) of cells (i.e., MES-SA cells and Dx5 cells) screened, isolated and purified according to the method of the present invention in four subzones of the cell isolation zone. As shown in FIG. 7B, the percentage of live Dx5 cells increased from 32.0% (subzone 1) to 82.4% (subzone 4), whereas the percentage of dead cells decreased from 52.0% (subzone 1) to 11.8% (subzone 4). For the live MES-SA cells, the percentages of the cells in these 4 subzones were 16.0%, 12.5%, 4.8% and 5.9% for subzone 1, 2, 3, and 4, respectively. The majority of drug-treated dead cells in the 4 subzones were MES-SA cells, whereas only a minority were Dx5 cells, based on the results shown in FIG. 3A (i.e., 5.0 $\mu g\ ml^{-1}$ doxorubicin for 48 hours; dead cell percentage: 73.9% and 4.5% for dead MES-SA and Dx5 cells, respectively). Theoretically, for these dead cells, ABCB1 gene expression would not be detected. Therefore, the ABCB1 gene expression detected in the defined four subzones (FIG. 6B) was attributable to the live Dx5 and live MES-SA cells in these four subzones. Moreover, it was found in FIG. 7B that 48.0% of the cells (32.0% and 16.0% for the live Dx5 and live MES-SA cells, respectively) in subzone 1 were alive. Nevertheless, their ABCB1 gene expression was not detected in this example (FIG. 6B; subzone 1). This phenomenon could be explained by the fact that these cells might not have the ABCB1 gene inherently or might have little ABCB1 gene expression. As a result, these drug-treated cells were more susceptible to the cytotoxic effect of doxorubicin. This result demonstrates that the method of the present invention is indeed useful for screening, isolating and purifying drug-treated cells with various degrees of drug resistance gene expression.

Example 6

Figure 8A:
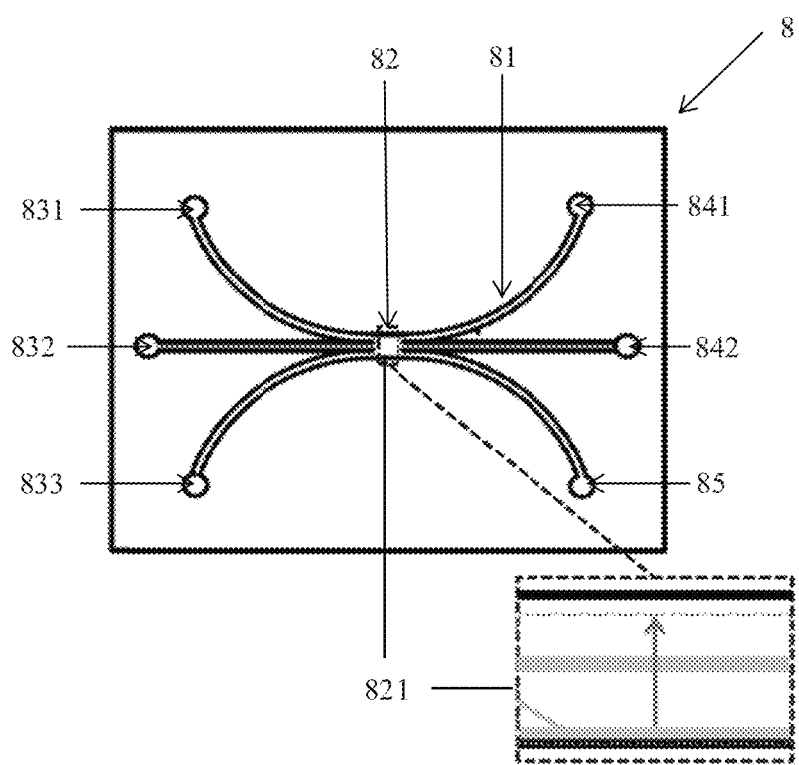
FIG. 8A is a schematic diagram showing the ODEP device of the present invention incorporating a laminar flow system.

Screening, Isolating and Purifying Latex Particles of Different Sizes According to the Method of the Present Invention FIG. 8A is a schematic diagram showing the ODEP device of the present invention incorporating a laminar flow system 8, which is designed to screen, isolate and purify latex particles having different sizes. As shown in FIG. 8A, the ODEP device incorporating the laminar flow system 8 comprises six side microchannels 81, a main microchannel 82, three target collection tanks (including a first target collection tank 831, a second target collection tank 832 and a third target collection tank 833), two laminar flow liquid injection tanks (including a first laminar flow liquid injection tank 841 and a second laminar flow liquid injection tank 842), and a sample loading tank 85. Each of the target collection tanks, laminar flow liquid injection tanks, and the sample loading tank 85 are disposed at the end of each of the side microchannels 81. The main microchannel 82 has a length of 4.15 mm, a width of 1.35 mm, and a height of 50 μm. Each of the linear side microchannels of the second laminar flow liquid injection tank 842 and the second target collection tank 832 has a length of 10 mm, a width of 450 μm, and a height of 50 μm. Each of the curved side microchannels 81 of the first laminar flow liquid injection tank 841, the first target collection tank 831, the third target collection tank 833, and the sample loading tank 85 has an average length of 11.0 mm, a width of 450 μm, and a height of 50 μm. The main microchannel 82 is used to screen latex particles of different sizes. The side microchannels 81 are used to inject laminar flow liquid, inject a sample, and collect the separated latex particles. The main microchannel 82 defines an ODEP light image manipulation zone 821 for screening latex particles of different sizes based on ODEP mechanism. The ODEP light image manipulation zone 821 has a length of 4 mm, a width of 1.2 mm, and a height of 50 μm. The sample loading tank 85 is used to inject a sample to be purified and separated. The first laminar flow liquid injection tank 841 corresponds to the first target collection tank 831, the second laminar flow liquid injection tank 842 corresponds to the second target collection tank 832, and the sample loading tank 85 corresponds to the third target collection tank 833. The design facilitates the construction of a stable three-laminar flow system in the ODEP device incorporating the laminar flow system 8 of the present invention, allowing different sizes of latex particles screened in the ODEP light image operating zone 821 to be separated and collected into different target collection tanks in response to fluid movement.

Figure 8B:
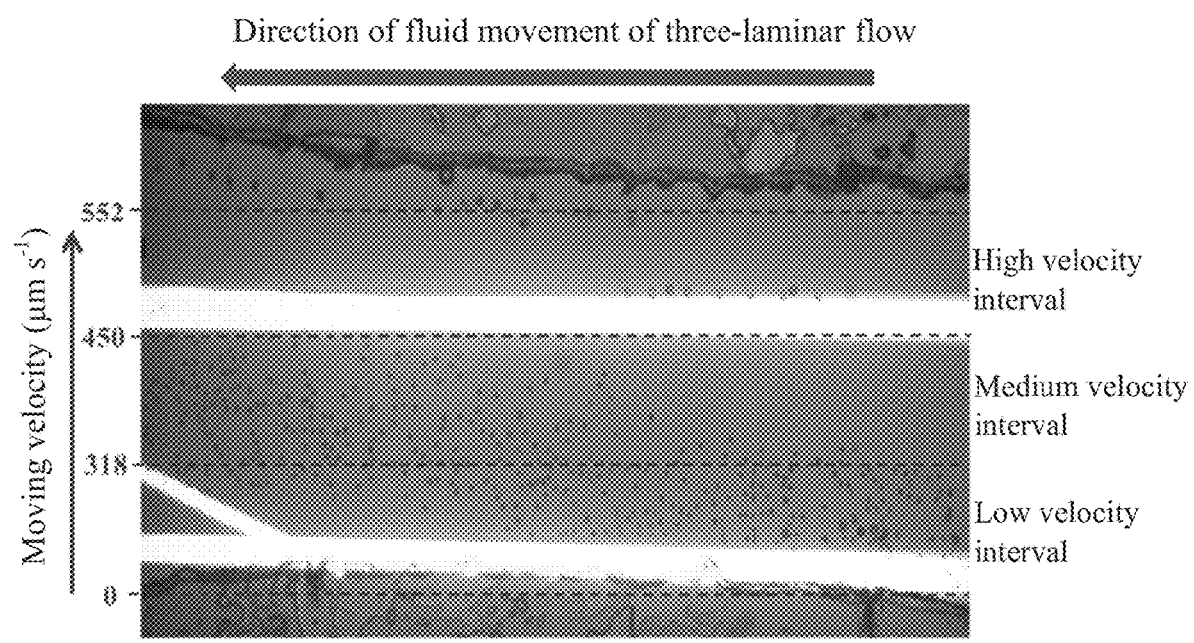
FIG. 8B is a schematic diagram showing the screening, isolation and purification of two different sizes of latex particles (i.e., particle diameters of 30 µm and 14.6 µm) performed in accordance with the method of the present invention.

FIG. 8B is a schematic diagram showing the screening, isolation and purification of two different sizes of latex particles (particle diameters of 30 μm and 14.6 μm) performed in accordance with the method of the present invention. It can be known by equation (I) that the intensity of the ODEP force has a positive correlation with the size of the manipulated particles, which makes the manipulating velocity of moving light images of large-sized particles to be greater than that of small-sized particles, so that different sizes of particles can be screened by a moving rectangular light bar (length: 4 mm; width: 100 μm) that changes from low velocity to high velocity. Subsequently, by utilizing the characteristics of the laminar flow in the flow channel, different sizes of particles can be separated and collected into corresponding target collection tanks. In this experiment, when the electrical parameter condition is set to 10V and 100 kHz and the background solution is sucrose solution with 5% bovine serum albumin (BSA), a moving rectangular light bar with a uniform acceleration (acceleration: 110.4 μm $s^{-2}$; starting velocity: 0 μm $s^{-1}$; terminal velocity: 552 μm $s^{-1}$) was utilized to separate and purify 14.6 μm and 30 μm latex particles mixed in equal amount to different velocity intervals. In addition, the establishment of a three-laminar flow system relies on maintaining the flow rate of the injected fluid at a constant velocity (the liquid entering velocities of the first laminar flow liquid injection tank 841, the second laminar flow liquid injection tank 842, and the sample loading tank 85 are all 0.5 μl $min^{-1}$), which allows the three fluids to maintain parallel movement and the same fluid width flowing into different target collection tanks respectively, thus establishing high, medium, and low velocity intervals for collecting the particles with different sizes in the main channel (the differences between high, medium, and low velocity intervals represent the different velocity ranges of moving rectangular light bars). According to the direction of fluid movement (from right to left) shown in FIG. 8B, samples of 14.6 μm and 30 μm latex particles mixed in equal amount are introduced from the sample loading tank 85 into the low velocity interval of the ODEP light image manipulation zone 821 (0-318 μm $s^{-1}$). Subsequently, in the ODEP light image manipulation zone 821, a plurality of moving rectangular light bars with uniform acceleration are used to screen the latex particles of different sizes, and the screened latex particles are purified and separated into corresponding target collection tanks through the three-laminar flow. Large-sized latex particles (30 μm) are gathered into the high velocity interval (450-552 μm $s^{-1}$) due to the high intensity of the ODEP force generated on particles, and are collected to the first target collection tank 831. Conversely, small-sized latex particles (14.6 μm) are gathered into the medium velocity interval (318-450 μm s) due to the low intensity of the ODEP force generated on particles, and are collected to the second target collection tank 832. The third target collection tank 833 can be used to collect the third sample. However, since only two different sizes of latex particles are used in this example, the third target collection tank 833 is only used to maintain the stable three-laminar flow in this example (no latex particles inflow). The result of this example demonstrates that the method of the present invention can be used to screen, isolate and purify latex particles of different sizes.

In summary, the method for screening, isolating and purifying an analyte has the effect of simple and flexible operation, and high sensitivity, resolution, and precision. The method of the present invention can successfully screen the analytes via the size or the viability degree. Meanwhile, the method of the present invention can isolate and purify the analytes with different sizes or various degrees of viability to facilitate identification of cell populations with different environmental tolerances (e.g., drug resistance, radiation resistance, oxidative stress resistance, toxic chemical resistance, or cell apoptosis degrees) or different sizes of chemical material particles or metal particles. Furthermore, the method of the present invention can be used as a front-end screening instrument for subsequent research analysis or clinical applications and can make immediate adjustments according to different sample conditions, which are conducive to the development of precision medicine. In addition, according to pretreatment conditions, the cells isolated and purified by the method of the present invention can be used to investigate the cell populations with the different expression of environmental tolerances, such as drug resistance, radiation resistance, oxidative stress resistance, toxic chemical resistance, or cell apoptosis. On the other hand, the method of the present invention can be utilized to investigate whether the results of cell sorting caused by different environmental conditions will have differences in gene expression or molecular biological mechanism. Therefore, the present invention has important application value in both clinical medicine and fundamental research.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for screening, isolating and purifying an analyte with an optically induced-electrophoresis (ODEP) device, comprising the steps of:
   (a) performing a treatment on the analyte to obtain a treated analyte, wherein the treatment comprises a background solution directed towards the analyte, and produces a difference in size or degree of cell viability in the analyte;
   (b) introducing the treated analyte into the optically induced-electrophoresis device, wherein the optically induced-electrophoresis device comprises a main microchannel, at least one side microchannel, at least one target collection tank, and an optically-induced dielectrophoretic force light image module having a controllable velocity, wherein the optically-induced dielectrophoretic force light image module screens the treated analyte in the main microchannel in order to separate the treated analyte according to its size or degree of cell viability into at least one target using a separation and purification method; and (c) collecting the at least one target into the at least one target collection tank; wherein the optically-induced dielectrophoretic force light image module comprises at least one moving light bar selected from the group consisting of: first moving light bar, second moving light bar, and a combination thereof;

wherein the at least one first moving light bar has a moving velocity of a light image ranging from 0.01 pm/s to 1 cm/s, the moving velocity of the light image is a variable speed, and the moving velocity of the light image increases when the at least one first moving light bar moves a predetermined distance;

wherein the optically-induced dielectrophoretic force light image module comprises at least one second moving light bar, the at least one second moving light bar has a moving velocity of a light image ranging from 0.01 pm/s to 1 cm/s, the moving velocity of the light image among the at least one second moving light bar is different, and the moving velocity of the light image is a constant speed;

wherein the size or degree of cell viability of the analyte is screened, and the analyte having different sizes or degrees of viability is isolated and purified by the ODEP device; and wherein cells having different degrees of environmental tolerance gene expression are screened, isolated and purified depending on their environmental stimulus-induced differences of cell viability degrees by the ODEP device.

2. The method according to claim 1, wherein the analyte is a microorganism, a plant cell, an animal cell, a chemical material particle or a metal particle.

3. The method according to claim 2, wherein the treatment is a treatment capable of inducing a viability difference of cells, or a treatment capable of inducing a size difference of the cells, the chemical material particle or the metal particle.

4. The method according to claim 3, wherein the treatment is a drug treatment, a radiation treatment, an oxidative stress treatment, a toxic chemical treatment, or a cell apoptosis treatment when the treatment is capable of inducing the degree of viability difference of cells, wherein the cell apoptosis treatment induces apoptosis.

5. The method according to claim 1, wherein the separation and purification method is performed by a physical drive selected from the group consisting of: a fluid drive, an electromagnetic drive, an optical drive, and an optically-induced dielectrophoretic force drive.

6. The method according to claim 1, wherein the environmental tolerance gene is a drug-associated gene, a radiation-associated gene, an oxidative stress-associated gene, a toxic chemical-associated gene, or a cell apoptosis-associated gene.

* * * * *